(12) United States Patent
Ibuki et al.

(10) Patent No.: US 10,741,095 B2
(45) Date of Patent: Aug. 11, 2020

(54) TEACHING COMPATIBILITY DETERMINING DEVICE, SYSTEM, METHOD AND RECORDING MEDIUM

(71) Applicant: OMRON Corporation, Kyoto (JP)

(72) Inventors: Hiroyuki Ibuki, Ichinomiya (JP); Tatsuya Adachi, Ichinomiya (JP)

(73) Assignee: OMRON Corporation, Kyoto (JP)

( * ) Notice: Subject to any disclaimer, the term of this patent is extended or adjusted under 35 U.S.C. 154(b) by 215 days.

(21) Appl. No.: 15/744,842

(22) PCT Filed: Sep. 30, 2016

(86) PCT No.: PCT/JP2016/078970
§ 371 (c)(1),
(2) Date: Jan. 15, 2018

(87) PCT Pub. No.: WO2017/057657
PCT Pub. Date: Apr. 6, 2017

(65) Prior Publication Data
US 2018/0211557 A1    Jul. 26, 2018

(30) Foreign Application Priority Data
Oct. 1, 2015   (JP) .................................. 2015-195985

(51) Int. Cl.
*A63F 9/24*        (2006.01)
*G09B 19/00*       (2006.01)
(Continued)

(52) U.S. Cl.
CPC ............ *G09B 19/0038* (2013.01); *A61B 5/11* (2013.01); *A61B 5/112* (2013.01); *A61B 5/1122* (2013.01);
(Continued)

(58) Field of Classification Search
CPC ..... G09B 19/0038; A61B 5/11; A61B 5/4833; A61B 5/1122; A61B 5/1124
See application file for complete search history.

(56) References Cited

U.S. PATENT DOCUMENTS 5,103,408 A * 4/1992 Greenberg ............... A61B 5/18
434/323
5,524,645 A * 6/1996 Wills ....................... A61H 1/02
128/898

(Continued)

FOREIGN PATENT DOCUMENTS

CN         102350040      2/2012
CN         102836543      12/2012
(Continued)

OTHER PUBLICATIONS

Office Action of China Counterpart Application, with English translation thereof, dated Feb. 22, 2019, pp. 1-10.

(Continued)

*Primary Examiner* — Steve Rowland
(74) *Attorney, Agent, or Firm* — JCIPRNET

(57) ABSTRACT

The present invention is provided with: a first detector (A) which detects, as an application result, whether a user could implement, as instructed, teaching content according to a program selected from a training menu; a second detector (B) which detects, as a compatibility result, whether effects of the teaching content were exhibited; a recording part (14) which cumulatively records the application result and the compatibility result as an execution result together with program identifying information; and a calculation part (13) which, on the basis of one or more than one execution results recorded in the recording part, calculates for each program, as a compatibility ratio, the ratio of the number of execution (Continued)

results having positive compatibility results to the number of execution results having positive application results.

12 Claims, 5 Drawing Sheets

(51) Int. Cl.
    *A61B 5/11*     (2006.01)
    *A61B 5/00*     (2006.01)
    *G09B 5/06*     (2006.01)
    *A63B 69/00*     (2006.01)

(52) U.S. Cl.
    CPC .......... *A61B 5/1124* (2013.01); *A61B 5/486* (2013.01); *A61B 5/4833* (2013.01); *A61B 5/6802* (2013.01); *A63B 69/0035* (2013.01); *G09B 5/06* (2013.01); *A61B 2503/10* (2013.01); *A61B 2562/0219* (2013.01)

(56) References Cited

U.S. PATENT DOCUMENTS

| | | | | |
|---|---|---|---|---|
| 5,860,939 | A * | 1/1999 | Wofford | A61B 5/0484 600/547 |
| 5,980,429 | A | 11/1999 | Nashner | |
| 6,632,158 | B1 * | 10/2003 | Nashner | A61B 5/1036 434/247 |
| 2005/0014113 | A1 | 1/2005 | Fleck et al. | |
| 2006/0025282 | A1 * | 2/2006 | Redmann | A61B 5/103 482/8 |
| 2007/0232455 | A1 | 10/2007 | Hanoun | |
| 2012/0191467 | A1 * | 7/2012 | LaPlante | G06Q 50/22 705/2 |
| 2012/0225413 | A1 * | 9/2012 | Kotranza | G09B 23/30 434/262 |
| 2014/0081661 | A1 * | 3/2014 | Fu | G06F 19/3481 705/3 |
| 2014/0234814 | A1 | 8/2014 | Krosky et al. | |
| 2016/0055442 | A1 * | 2/2016 | Chadwick | G06Q 10/06398 705/7.42 |
| 2018/0330810 | A1 * | 11/2018 | Gamarnik | G16H 20/30 |

FOREIGN PATENT DOCUMENTS

| | | |
|---|---|---|
| JP | 2009028459 | 2/2009 |
| JP | 2011078728 | 4/2011 |
| JP | 2012128798 | 7/2012 |
| JP | 2013066672 | 4/2013 |
| JP | 2013172135 | 9/2013 |
| JP | 2015054010 | 3/2015 |
| WO | 2009078114 | 6/2009 |
| WO | 2015110298 | 7/2015 |

OTHER PUBLICATIONS

"International Search Report (Form PCT/ISA/210) of PCT/JP2016/078970," dated Dec. 13, 2016, with English translation thereof, pp. 1-4.

"Written Opinion of the International Searching Authority (Form PCT/ISA/237) of PCT/JP2016/078970," dated Dec. 13, 2016, with English translation thereof, pp. 1-8.

Office Action of Japan Counterpart Application, with English translation thereof, dated Nov. 13, 2018, pp. 1-6.

"Search Report of Europe Counterpart Application", dated Apr. 29, 2019, p. 1-p. 9.

* cited by examiner

TRAINING MENU TABLE

| PROGRAM NAME | SENSOR A GROUP | SENSOR B GROUP |
|---|---|---|
| TURNING OF PELVIS | TURNING OF SCAPULA | TURNING OF PELVIS |
| STABILIZATION OF CENTER OF GRAVITY | FORWARD BENDING OF PELVIS | DEVIATION OF CENTER OF GRAVITY OF UPPER BODY |
| ⋮ | ⋮ | ⋮ |
| ⋮ | ⋮ | ⋮ |

FIG. 4

TRAINING RESULT TABLE

| PROGRAM NAME | USER ID | APPLICATION/ NON-APPLICATION | COMPATIBLE/ INCOMPATIBLE |
|---|---|---|---|
| TURNING OF PELVIS | 0001 | ○ | ○ |
| TURNING OF PELVIS | 0002 | ○ | × |
| TURNING OF PELVIS | 0003 | ○ | ○ |
| TURNING OF PELVIS | 0004 | × | — |
| TURNING OF PELVIS | 0005 | ○ | ○ |
| ... | ... | ... | ... |
| STABILIZATION OF CENTER OF GRAVITY | 0001 | ○ | ○ |
| STABILIZATION OF CENTER OF GRAVITY | 0002 | ○ | × |
| STABILIZATION OF CENTER OF GRAVITY | 0003 | × | — |
| ... | ... | ... | ... |

FIG. 5

USER REGISTRATION TABLE

| USER ID | HEIGHT | FLEXIBILITY OF SHOULDER |
|---------|--------|-------------------------|
| 0001 | 173cm | SOFTNESS |
| 0002 | 156cm | HARDNESS |
| 0003 | 168cm | ORDINARY |
| ⋮ | ⋮ | ⋮ |

FIG. 6

TEACHING COMPATIBILITY DETERMINING DEVICE, SYSTEM, METHOD AND RECORDING MEDIUM

CROSS-REFERENCE TO RELATED APPLICATION

This application is a 371 application of the international PCT application serial no. PCT/JP2016/078970, filed on Sep. 30, 2016, which claims the priority benefit of Japan application no. 2015-195985, filed on Oct. 1, 2015. The entirety of each of the abovementioned patent applications is hereby incorporated by reference herein and made a part of this specification.

TECHNICAL FIELD

The invention relates to a teaching compatibility determining device, a teaching compatibility determining system, a teaching compatibility determining method, a teaching compatibility determining program, and a recording medium recording the program that determines whether teaching content according to a program selected from a training menu is able to be executed and effects thereof are exhibited.

BACKGROUND ART

In the related art, a body state evaluating device that can detect a motion of a sample body with a three-axis acceleration sensor mounted thereon, measure and evaluate a physical state of the sample body, and provide an exercise prescription or an exercise menu for correcting a posture or the like has been proposed (for example, see Patent Literature 1).

The body state evaluating device is characterized by including a compensatory motion measuring means that measures a compensatory motion that accompanies a predetermined motion of a sample body and an evaluation means that evaluates a body physical state of the sample body on the basis of information on the compensatory motion measured by the compensatory motion measuring means.

A walking posture meter that can quantitatively evaluate whether a walking posture of a person is correct using a three-axis acceleration sensor and evaluate whether the center of gravity during walking leans forward/backward in a moving direction has also been proposed (for example, see Patent Literature 2).

The walking posture meter is a walking posture meter that evaluates a walking posture of a person to be measured and is characterized by including an acceleration sensor that is mounted on the center line of a waist of a person to be measured and a first computing part that computes at least one of a quantity indicating a degree by which the center of gravity of the person to be measured during walking leans forward in the moving direction with respect to the person to be measured and a quantity indicating a degree by which the center of gravity leans backward in the moving direction with respect to the person to be measured using a temporal change waveform of vertical-axis acceleration which is output from the acceleration sensor.

CITATION LIST

Patent Literature

[Patent Literature 1]
Japanese Patent Application Laid-Open No. 2011-078728

[Patent Literature 2]
Japanese Patent Application Laid-Open No. 2013-172135

SUMMARY OF INVENTION

Technical Problem

In a teaching site in sports and the like, examples of a problem on a player side include a problem in that a player does not specifically know what part of his or her body to train and a problem in that a player cannot assimilate many teachings after hearing them once. Examples of a problem on a coach side include a problem in that it is difficult to deliver a sense or a skill (tacit knowledge) to a player. As a result, the player cannot continue training and as a result can also lead to not advance.

Whether content taught by a coach is effective for a player is handled as an empirical rule. Whether the teaching content is effective for a player cannot be known in advance, and the player is trained with the teaching content without confidence.

For example, programs for improvement of a running form in a marathon are proposed:

(1) turning of the pelvis; and
(2) stabilization of the center of gravity.

Among these, the "turning of the pelvis" in (1) is a program for realizing a running motion using inner muscles and improves the running form as follows.

(a) The scapula is drawn to the center of the back.
(b) The same side of the pelvis is turned forward therewith.
(c) A leg moves forward quickly with the turning of the pelvis.

When a player grows accustomed to this running form, the player can exhibit muscular power using a plurality of muscles of the body and can reduce muscle fatigue of a specific part such as the legs.

When a coach teaches a player this content, the purpose of the teaching is (b), but the player has difficulty in understanding what the player should specifically do even when the coach instructs him or her to "turn his or her waist." Therefore, as a specific improvement for the running form for achieving (b), the coach gives the instruction of (a) to the player (for example, "draw your scapula back").

Though the player tries or intends to improve his or her running form in accordance with the instruction, he or she does not know himself of herself whether improvement is satisfactorily achieved and stays at a degree that is only advised later by the coach.

The "stabilization of the center of gravity" in (2) is a program for realizing a running motion with reduced imbalance in movement of the center of gravity and is for improving a running form to keep a forward-bending posture of the pelvis while recognizing a lower part of the abdomen (a slightly lower part of the navel).

When a waist height can be maintained by the forward-bending posture of the pelvis, it is possible to achieve stable running with reduced movement of the center of gravity of the body and to reduce energy loss.

In this way, a specific instruction of the teaching content according to a program in a training menu is generally different from an effect of the teaching that one actually wants to check. However, Patent Literature 1 and Patent Literature 2 do not disclose separate evaluation of an instruction and an effect.

Sensors which have hit the market carry out only simple visualization such as sensing a state of a waist for turning of the waist or sensing the position of the center of gravity for stabilization of the center of gravity. For example, a golf swing sensor only records swing data in detail using a dedicated application and uses the swing data for improvement of a swing.

Image diagnosis based on motion capture using a plurality of cameras and a plurality of markers which are attached to parts of the body are commercialized as a method of really analyzing a body motion during an exercise. However, since special facilities or high-cost equipment is necessary, this technology is not readily available to all and there is a problem in that an exercise in an environment other than a normal environment does not necessarily provide a natural motion.

In consideration of the above-mentioned problems in the related art, an object of the invention is to provide a teaching compatibility determining device, a teaching compatibility determining system, a teaching compatibility determining method, a teaching compatibility determining program, and a recording medium recording the program that can understand in real time whether teaching content based on a program selected from a training menu is executed as instructed and whether effects of the teaching content are exhibited and can predict effects of various types of teaching content on the basis of cumulative results.

Solution to Problem

In order to achieve the above-mentioned object, a teaching compatibility determining device according to the invention is characterized by including: a first detector configured to detect whether a user is able to execute teaching content according to a program selected from a training menu as instructed as an application result; a second detector configured to detect whether effects of the teaching content are exhibited as a compatibility result; a recording part configured to cumulatively record the application result and the compatibility result together with program identification information as an execution result; and a computing part configured to calculate a ratio of the number of execution results in which the compatibility result is positive to the number of execution results in which the application result is positive as a compatibility ratio for each program on the basis of one or more than one execution results recorded on the recording part.

Here, examples of the first detector and the second detector include sensors that detect accelerations and angular velocities of three axes, but the invention is not limited thereto.

According to the teaching compatibility determining device having the above-mentioned configuration, it is possible to understand in real time whether it is able to execute the teaching content according to a program selected from the training menu as instructed and whether effects of the teaching content are accordingly exhibited. In this way, by one by one executing each program into which a motion or capability is decomposed in a concentrated manner, it is possible to achieve very efficient training. By accumulating the execution results of the teaching content according to the program, it is possible to predict effects of each teaching content in advance and to train with the teaching content with confidence.

In the teaching compatibility determining device according to the invention, the computing part may extract a program suitable for the user from the training menu on the basis of the compatibility ratio for each program and present the extracted program to the user. The computing part may calculate a ratio of the number of execution results in which the application result is positive to the number of corresponding execution results for each program as an application ratio on the basis of one or more than one execution results recorded on the recording part and present a program suitable for the user on the basis of the application ratio and/or the compatibility ratio for each program. The computing part may extract another program suitable for the user from the training menu on the basis of the application ratio and/or the compatibility ratio for each program and present the extracted program to the user when the application result is not positive within a predetermined period of time after the user starts execution of the selected program. The recording part may record user identification information and attribute information of the user.

In the teaching compatibility determining device according to the invention, the computing part may analyze a correlation between items of the attribute information and the compatibility ratio for each program on the basis of one or more than one execution results recorded on the recording part, the identification information of the execution results, and the attribute information of the user. The computing part may extract another program suitable for the user from the training menu on the basis of the correlation and present the extracted program to the user.

Alternatively, a teaching compatibility determining system according to the invention is characterized by including: a first detector configured to detect whether a user is able to execute teaching content according to a program selected from a training menu as instructed as an application result; a second detector configured to detect whether effects of the teaching content are exhibited as a compatibility result; a recording part configured to cumulatively record the application result and the compatibility result together with program identification information as an execution result; and a computing part configured to calculate a ratio of the number of execution results in which the compatibility result is positive to the number of execution results in which the application result is positive as a compatibility ratio for each program on the basis of one or more than one execution results recorded on the recording part.

Alternatively, a teaching compatibility determining method according to the invention is characterized by including: a first detecting step of detecting whether a user is able to execute teaching content according to a program selected from a training menu as instructed as an application result; a second detecting step of detecting whether effects of the teaching content are exhibited as a compatibility result; a recording step of cumulatively recording the application result and the compatibility result together with program identification information as an execution result; and a computing step of calculating a ratio of the number of execution results in which the compatibility result is positive to the number of execution results in which the application result is positive as a compatibility ratio for each program on the basis of one or more than one execution results recorded in the recording step.

According to the teaching compatibility determining method having the above-mentioned configuration, it is possible to understand in real time whether it is able to execute the teaching content according to a program selected from the training menu as instructed and whether effects of the teaching content are accordingly exhibited. In this way, by one by one executing each program into which a motion or capability is decomposed in a concentrated manner, it is possible to achieve very efficient training. By accumulating the execution results of the teaching content according to the program, it is possible to predict effects of each teaching content in advance and to train with the teaching content with confidence.

Alternatively, a teaching compatibility determining program according to the invention causes a computer to perform the above-mentioned teaching compatibility determining method.

According to the teaching compatibility determining program having the above-mentioned configuration, the teaching compatibility determining method according to the invention can be embodied in any place as long as there is a computer environment in which a program is executable. When the teaching compatibility determining program is set to be executable by a general-purpose computer in advance, it is not necessary to prepare a dedicated computer environment for embodying the teaching compatibility determining method according to the invention and it is possible to enhance usefulness of the teaching compatibility determining program according to the invention.

Alternatively, a recording medium according to the invention, recording a teaching compatibility determining program, is a computer-readable recording medium and is characterized by recording the foregoing teaching compatibility determining program.

According to the recording medium having the above-mentioned configuration that recording the teaching compatibility determining program, the teaching compatibility determining method according to the invention can be easily embodied in various places or environments and can be provided at a low cost, and it is possible to improve the teaching compatibility determining method according to the invention.

Advantageous Effects of Invention

With the teaching compatibility determining device, the teaching compatibility determining system, and the teaching compatibility determining method according to the invention, it is possible to understand in real time whether it is able to execute the teaching content according to a program selected from the training menu as instructed and whether effects of the teaching content are accordingly exhibited. In this way, by one by one executing each program into which a motion or capability is decomposed in a concentrated manner, it is possible to achieve very efficient training. By accumulating the execution results of the teaching content according to the program, it is possible to predict effects of each teaching content in advance and to train with the teaching content with confidence.

With the teaching compatibility determining program according to the invention, the teaching compatibility determining method according to the invention can be embodied in any place as long as there is a computer environment in which a program is executable. When the teaching compatibility determining program is set to be executable by a general-purpose computer, it is not necessary to prepare a dedicated computer environment for embodying the teaching compatibility determining method according to the invention and it is possible to enhance usefulness of the teaching compatibility determining program according to the invention.

With the recording medium recording the teaching compatibility determining program according to the invention, the teaching compatibility determining method according to the invention can be easily embodied in various places or environments and can be provided at a low cost, and it is possible to improve the teaching compatibility determining method according to the invention.

BRIEF DESCRIPTION OF DRAWINGS

FIG. 4 is a diagram illustrating a program which is registered in the training menu table 20.

FIG. 5 is a diagram illustrating a training result table which is recorded in a table recording part 14.

FIG. 6 is a diagram illustrating a user registration table which is recorded in the table recording part 14.

DESCRIPTION OF EMBODIMENTS

Hereinafter, embodiments of the invention will be described with reference to drawings.
<Configuration of Embodiment>

Figure 1:
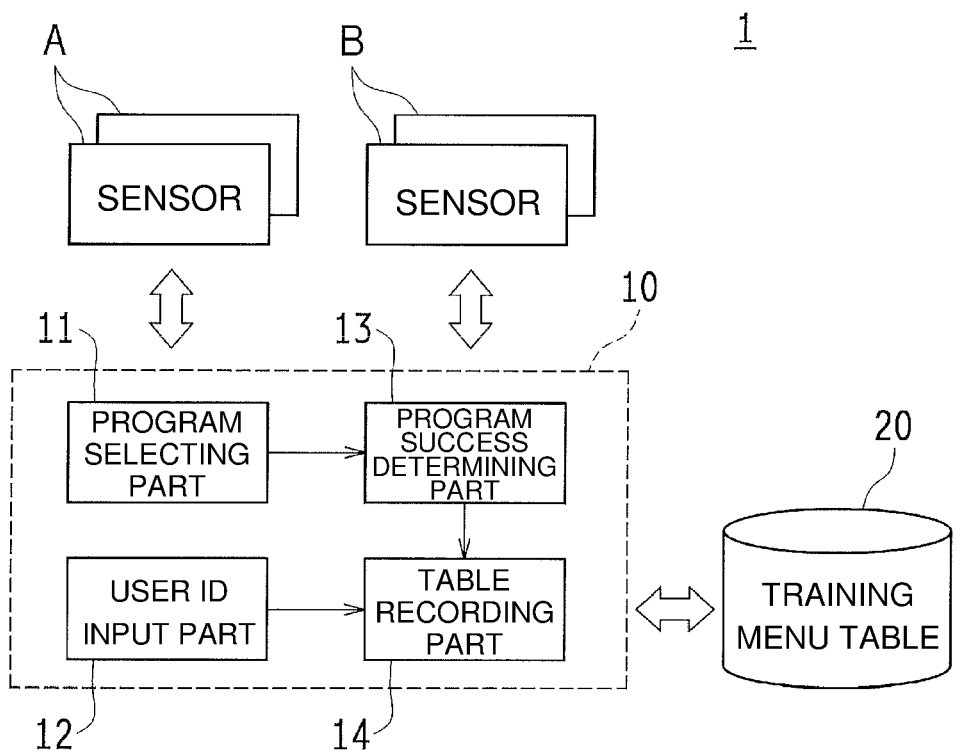
FIG. 1 is a schematic block diagram of a teaching compatibility determining device 1 according to an embodiment of the invention.
Figure 2:
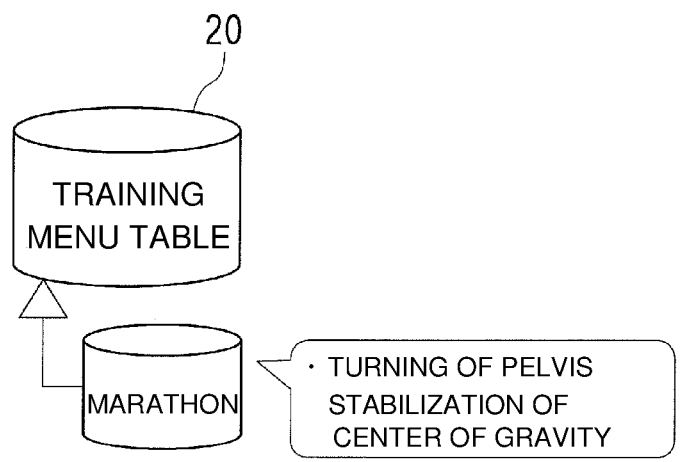
FIG. 2 is a diagram schematically illustrating a structure of a training menu table 20 which is used for the teaching compatibility determining device 1.

FIG. 1 is a schematic block diagram of a teaching compatibility determining device 1 according to an embodiment of the invention. FIG. 2 is a diagram schematically illustrating a structure of a training menu table 20 which is used for the teaching compatibility determining device 1.

As illustrated in FIG. 1, the teaching compatibility determining device 1 includes one or more than one sensors A that detect whether a user is able to execute teaching content according to a program selected from a training menu as instructed, one or more than one sensors B that detect whether effects of the teaching content are exhibited, a training menu table 20 that registers various programs in the training menu, and a determining device body 10 that is connected to the sensor A and the sensor B in a short-range wireless communication manner and is wirelessly connected to the training menu table 20.

Examples of hardware of the sensor A and the sensor B include wireless sensors having a three-axis acceleration sensor and a three-axis angular velocity sensor incorporated therein. It is preferable that the sensors have measurement accuracy with which an acceleration or an angular velocity corresponding to an angle variation of about 1 to 2 degrees. It is preferable that the sensors have a small size and a small weight such that a motion of a user is not prevented as much as possible when the sensors are attached to measure movements of parts of the user's body. An example of the wireless communication system is Bluetooth (registered trademark of U.S. Bluetooth Sig., Inc.), particularly, Bluetooth Low Energy with very low power (also referred to as Bluetooth LE or BLE), but is not limited thereto.

But the sensor A and the sensor B are not limited thereto. A biosensor such as a pressure sensor, a blood sugar level sensor, a respiration sensor, or an oxygen saturation level sensor (a pulse oximeter) may be used. Sensors of a wired type are not excluded.

The sensor A is used to detect whether the user is able to execute teaching content according to a program selected from the training menu as instructed. For example, when the selected program is "turning of the pelvis" in an event of "marathon," the sensor A is attached to the vicinity of the user's right and left scapulae and detects an angle by which the scapulae are drawn to the center of the back during running. Through comparison of the detected angle with a predetermined threshold value, it is possible to determine whether the user is able to execute the teaching content as instructed. Here, whether the teaching content can be executed as instructed is referred to as an "application result" with a meaning indicating whether the teaching content is applied to the user.

The sensor B is used to detect whether effects of the teaching content according to the program selected from the training menu are exhibited. For example, similarly to the above description, when the selected program is "turning of the pelvis" in an event of "marathon," the sensor B is attached to the vicinity of the user's tailbone and detects a turning angle of the pelvis during running. Through comparison of the detected turning angle with a predetermined threshold value, it is possible to determine whether the effects of the teaching content are exhibited for the user. Here, whether the effects of the teaching content are exhibited is referred to as a "compatibility result" with a meaning indicating whether the teaching content is compatible with the user.

The training menu table 20 is a database in which various programs are registered for each training event as a training menu as illustrated in FIG. 2. For example, in the event of "marathon," running form improvement programs such as "turning of the pelvis" and "stabilization of the center of gravity" are registered. It is preferable that what kind of types of sensors and how many numbers of sensors are specifically used as the sensor A and the sensor B, sites of a user's body to which the sensors should be attached, and specific instructions of the teaching content, and the like be registered together for each program.

In this embodiment, on the assumption that a plurality of users simultaneously use the programs, the training menu table 20 is disposed in a server and the determining device body 10 accesses the training menu table 20 via a network. The invention is not limited to this configuration, but the training menu table 20 may be disposed in the determining device body 10.

The determining device body 10 includes a program selecting part 11 that selects one program from a preliminarily prepared training menu, a user ID input part 12 that is used to input a user ID for identifying a user, a program success determining part 13 that determines whether execution of a program has succeeded on the basis of detection results (an application result and a compatibility result) of the sensor A and the sensor B when the program selected by the program selecting part 11 is executed by a user, and a table recording part 14 that cumulatively records the determination result of the program success determining part 13 together with at least the user ID input via the user ID input part 12. These parts do not need to be incorporated into the determining device body 10. For example, the program success determining part 13 or the table recording part 14 may be disposed in a server, the sensor A and the sensor B are also included and a teaching compatibility determining system may be configured.

The determining device body 10 further includes a short-range wireless communication part that enables short-range wireless communication with the sensor A and the sensor B, a communication part that enables reading and writing by wireless with the training menu table 20, a touch panel that also serves as a display part and an operation part, an LED that realizes visual display such as lighting or blinking, a speaker that realizes auditory display such as issuance of warning sound, and a control part (CPU) that controls the parts (none of which is illustrated).

The determining device body 10 always monitors the detection results of the sensor A and the sensor B such that a user can understand in real time whether the teaching content is executed as instructed during training, and issues warning sound or the like from the speaker when the detection result of the sensor A indicates that the teaching content is not executed as instructed. At the same time, blinking of the LED or the like may be performed. On the contrary, only when the detection result of the sensor A indicates that the teaching content is executed as instructed, predetermined notification sound may be issued.

A smartphone or a wearable computer which can be worn by a user during training can be preferably used as a specific example of the determining device body 10, but the invention is not limited thereto. For example, in the case of indoor training without much movement, a tablet terminal or a notebook PC may be used.

<Teaching Compatibility Determining Process>

Figure 3:
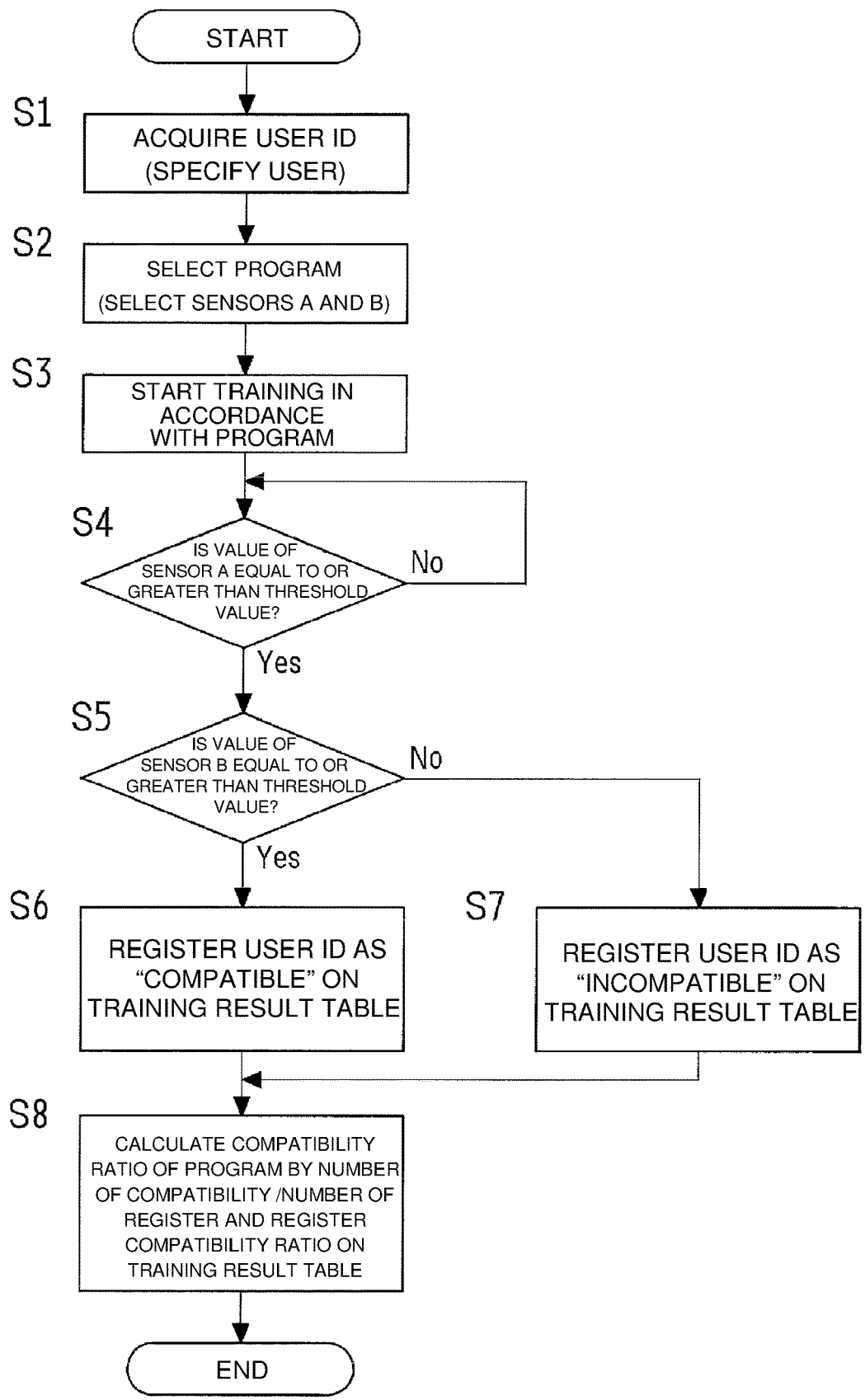
FIG. 3 is a flowchart schematically illustrating a teaching compatibility determining process which is performed by a control part when training is carried out using the teaching compatibility determining device 1.

FIG. 3 is a flowchart schematically illustrating a teaching compatibility determining process which is performed by the control part when training is carried out using the teaching compatibility determining device 1. FIG. 4 is a diagram illustrating programs which are registered in the training menu table 20. FIG. 5 is a diagram illustrating a training result table which is recorded in the table recording part 14. FIG. 6 is a diagram illustrating a user registration table which is recorded in the table recording part 14.

The teaching compatibility determining process is performed by executing a teaching compatibility determining program (the "program" here is software and has a different meaning from the "program" in the training menu) which is written to the control part. The teaching compatibility determining program can be provided using a CD-ROM or a USB memory on which the program is recorded or via a network or the like.

When it is intended to start training, first, a user performs an operation of inputting his or her user ID which is previously allocated to the determining device body 10. Accordingly, the control part of the determining device body 10 can acquire the user ID and can specify the user (Step S1).

As illustrated in FIG. 6, the user ID of each user and attribute information of the corresponding user (for example, body information which includes a height and flexibility of the shoulder herein) as a user registration table in the table recording part 14 in advance. The body information may include sex, age, weight, and the like, but is not limited thereto. A part of the body information may be acquired by automatic measurement to implement.

Then, the user performs an operation of designating a desired program from the training menu registered in advance in the training menu table 20. Accordingly, the control part selects the designated program from the training menu table 20, selects the sensor A and the sensor B corresponding to the program, and determine what types sensors and how many sensors should be used and to what positions the sensors should be attached (Step S2).

For example, as illustrated in FIG. 4, at least two programs corresponding to the event of "marathon" are registered in the training menu table 20, and when the user performs an operation of designating "turning of the pelvis" among the programs, the control part selects a necessary number of specific sensors that can measure "turning of the scapula" as the sensor A and a necessary number of specific sensors that can measure "turning of the pelvis" as the sensor B and determines to what positions of the body the sensors should be attached.

At this time, attachment positions of the sensor A and the sensor B or specific instructions of the teaching content may be displayed on the touch panel of the determining device body 10, or explanation of the teaching content may be output by voice.

The user attaches the selected sensor A and the selected sensor B to parts of the body and starts training in accordance with instructions of the teaching content of the designated program (Step S3).

The control part always monitors each of the detection results of the selected sensor A and the selected sensor B and first determines whether the detection result of the sensor A indicates that the teaching content can be executed as instructed, specifically, whether the detection result of the sensor A is equal to or greater than a predetermined threshold value (Step S4). Here, whether to be equal to or greater than the threshold value is used for the determination, but whether a measured value is equal to or less than a threshold value, or is within a predetermined range may be determined in various manners depending on a used sensor or a measuring object. This is the same for determination of the sensor B which will be described later.

When it is determined that the detection result is equal to or greater than the threshold value, process to next step S5. When it is determined that the detection result is less than the threshold value, the control part goes back and continues to monitor the sensor A and the sensor B. At this time, warning sound indicating that the teaching content is not executed as instructed is issued from the speaker of the determining device body 10. The user needs to continuously execute training until the warning sound stops.

When the user executes the teaching content as instructed and the detection result of the sensor A is equal to or greater than the threshold value, the control part then determines whether the detection result of the sensor B indicates that effects of the teaching content are exhibited, specifically, whether the detection result of the sensor B is equal to or greater than a predetermined threshold value (Step S5).

When it is determined that the determination result is equal to or greater than the threshold value, it means that the user can execute the teaching content as instructed (the application result is "positive") and the effects of the teaching content are exhibited (the compatibility result is "positive"), and thus the teaching content is compatible with the user. Therefore, the program name, the user ID, the application result (O=positive), and the compatibility result (O=positive) are cumulatively recorded on the table recording part 14 like first, third, fifth, and seventh records in the training result table illustrated in FIG. 5 (Step S6).

On the other hand, when it is determined in Step S5 that the detection result is less than the threshold value, it means that the user can execute the teaching content as instructed (the application result is "positive") but the effects of the teaching content are not exhibited (the compatibility result is "negative"), and thus the teaching content is not compatible with the user. Therefore, the program name, the user ID, the application result (O=positive), and the compatibility result (X=negative) are cumulatively recorded on the table recording part 14 like second and eighth records in the training result table illustrated in FIG. 5 (Step S7).

When processing to any one of Step S6 and Step S7, a "compatibility ratio" which is a ratio of the "number of records of which the compatibility result is registered as O (positive)" to the "number of records of which the application result is registered as O (positive)" is calculated for the records recorded on the training result table for each program and is recorded on the table recording part 14 (Step S8).

For example, as illustrated in FIG. 5, since the number of records of which the program name as the program identification information is "turning of the pelvis" and the application result is O (positive) is four and the number of records of which the compatibility result is O (positive) is three, the compatibility ratio is 3/4=75%. Since the number of records of which the program name is "stabilization of the center of gravity" and the application result is O (positive) is two and the number of records of which the compatibility result is O (positive) is one, the compatibility ratio is 1/2=50%.

An "application ratio" which is a ratio of the "number of records of which the application result is registered as O (positive) to the corresponding total number of records may be calculated for each program for the records recorded on the training result table and may be recorded on the table recording part 14.

For example, as illustrated in FIG. 5, since the total number of records of which the program name is "turning of the pelvis" is five and the number of records of which the application result is O (positive) is four, the application ratio is 4/5=80%. Since the total number of records of which the program name is "stabilization of the center of gravity" is three and the number of records of which the application result is O (positive) is two, the application ratio is 2/3≈67%.

According to the above-mentioned teaching compatibility determining device 1, a user can understand in real time whether the user can execute the teaching content according to a program selected from the training menu as instructed and whether effects of the teaching content are accordingly exhibited during execution of the teaching content according to the program. In this way, by one by one executing programs into which a motion or capability is decompose in a concentrated manner, it is possible to get very efficient training. By accumulating the execution results of the teaching content according to the program, it is possible to predict an effect of each teaching content in advance and a user can train with the teaching content with confidence.

<Modified Example of Teaching Compatibility Determining Process>

In Step S2, on the control part side, it may automatically select or may present candidates to the user to select one on the basis of such as details of existing records recorded on the training result table or body information of the user recorded on the user registration table.

When it is determined in Step S4 that the detection result of the sensor A is not equal to or greater than the threshold value within a predetermined period of time (a predetermined time or a predetermined repetition frequency), it means that the user cannot execute the teaching content as instructed and the teaching content is not compatible with the user. In this case, repetition of Step S4 is stopped, and the program name, the user ID, the application result (X=negative), and the compatibility result (-=undetermined) may be cumulatively recorded on the table recording part 14 like fourth and ninth records in the training result table illustrated in FIG. 5 and then the teaching compatibility determining process may end.

When the number of existing records recorded on the training result table increases, for example, it is possible to understand whether each program is likely to be effective for many persons or whether the number of persons for which the program is effective is small through comparison of the compatibility ratio for each program. Accordingly, in Step S2, a program which is effective for many persons can be presented as a candidate to the user.

When the compatibility ratio for each program is calculated with reference to a user's body information recorded in the user registration table and using only the existing records extracted on the basis of the body information as a population, it is possible to confirm a correlation between the body information and the compatibility ratio. By performing this process while changing the method of extracting a population, for example, it is possible to understand items of the body information which has a large influence on the compatibility ratio and to analyze causes for hindering compatibility (why the effects of the teaching content are not exhibited).

If the cause analysis progresses, a program which is predicted to be most effective on the basis of the user's body information can be presented as a candidate in Step S2. When it is determined in Step S4 that the detection result of the sensor A is not equal to or greater than the threshold value within a predetermined period of time, it can return to Step S2 and a next preferred program can be presented as a candidate instead of ending the teaching compatibility determining process.

Alternatively, classification of the difficulty level of the program becomes possible such as a program which can be expected to be very effective but of which the compatibility ratio is low can be classified into "advance class", a program which cannot be expected so much to be effective but of which the compatibility ratio is higher can be classified into "elementary class", and a program therebetween can be classified into "intermediate class". In Step S2, useful reference information can be presented when the user selects a program. As for a user for which a program is effective and the teaching compatibility determining process has ended through Step S6, another program of a higher class of the difficulty level can be presented as a candidate.

The invention can be embodied in various forms without departing from the gist or main features thereof. Accordingly, the above-mentioned embodiments or examples are only simple examples in view of all viewpoints, and should not be analyzed to be restrictive. The scope of the invention is defined by the appended claims, and is not constrained by details of the specification. All modifications or changes belonging to the equivalent scope of the claims are included in the scope of the invention.

The invention claimed is:

1. A teaching compatibility determining device comprising:
    a first detector configured to detect whether a user is able to execute teaching content according to a program selected from a training menu as instructed as an application result;
    a second detector configured to detect whether effects of the teaching content are exhibited as a compatibility result;
    a recording part configured to cumulatively record the application result and the compatibility result together with program identification information as an execution result; and
    a computing part configured to calculate a ratio of the number of execution results in which the compatibility result is positive to the number of execution results in which the application result is positive as a compatibility ratio for each program on the basis of one or more than one execution results recorded on the recording part,
    wherein the computing part calculates a ratio of the number of execution results in which the application result is positive to the number of corresponding execution results for each program as an application ratio on the basis of one or more than one execution results recorded on the recording part and presents a program suitable for the user on the basis of the application ratio and/or the compatibility ratio for each program, and
    wherein the computing part extracts another program suitable for the user from the training menu on the basis of the application ratio and/or the compatibility ratio for each program and presents the extracted program to the user when the application result is not positive within a predetermined period of time after the user starts execution of the selected program.

2. The teaching compatibility determining device according to claim 1, wherein the computing part extracts a program suitable for the user from the training menu on the basis of the compatibility ratio for each program and presents the extracted program to the user.

3. The teaching compatibility determining device according to claim 1, wherein the recording part records user identification information and attribute information of the user.

4. The teaching compatibility determining device according to claim 3, wherein the computing part analyzes a correlation between items of the attribute information and the compatibility ratio for each program on the basis of one or more than one execution results recorded on the recording part, the identification information of the execution results, and the attribute information of the user.

5. The teaching compatibility determining device according to claim 4, wherein the computing part extracts another program suitable for the user from the training menu on the basis of the correlation and presents the extracted program to the user.

6. The teaching compatibility determining device according to claim 1, wherein the first detector and the second detector are sensors that detect accelerations and angular velocities of three axes.

7. A teaching compatibility determining system comprising:
    a first detector configured to detect whether a user is able to execute teaching content according to a program selected from a training menu as instructed as an application result;
    a second detector configured to detect whether effects of the teaching content are exhibited as a compatibility result;
    a recording part configured to cumulatively record the application result and the compatibility result together with program identification information as an execution result; and
    a computing part configured to calculate a ratio of the number of execution results in which the compatibility result is positive to the number of execution results in which the application result is positive as a compatibility ratio for each program on the basis of one or more than one execution results recorded on the recording part,
    wherein the computing part calculates a ratio of the number of execution results in which the application result is positive to the number of corresponding execution results for each program as an application ratio on the basis of one or more than one execution results recorded on the recording part and presents a program suitable for the user on the basis of the application ratio and/or the compatibility ratio for each program, and wherein the computing part extracts another program suitable for the user from the training menu on the basis of the application ratio and/or the compatibility ratio for each program and presents the extracted program to the user when the application result is not positive within a predetermined period of time after the user starts execution of the selected program.

8. A teaching compatibility determining method comprising:
- a first detecting step of detecting whether a user is able to execute teaching content according to a program selected from a training menu as instructed as an application result;
- a second detecting step of detecting whether effects of the teaching content are exhibited as a compatibility result;
- a recording step of cumulatively recording the application result and the compatibility result together with program identification information as an execution result; and
- a computing step of calculating a ratio of the number of execution results in which the compatibility result is positive to the number of execution results in which the application result is positive as a compatibility ratio for each program on the basis of one or more than one execution results recorded in the recording step, wherein the computing step calculates a ratio of the number of execution results in which the application result is positive to the number of corresponding execution results for each program as an application ratio on the basis of one or more than one execution results recorded on the recording part and presents a program suitable for the user on the basis of the application ratio and/or the compatibility ratio for each program, and wherein the computing step extracts another program suitable for the user from the training menu on the basis of the application ratio and/or the compatibility ratio for each program and presents the extracted program to the user when the application result is not positive within a predetermined period of time after the user starts execution of the selected program.

9. A non-transitory computer-readable recording medium recording a teaching compatibility determining program, the teaching compatibility determining program causing a computer to perform the teaching compatibility determining method according to claim 8.

10. The teaching compatibility determining device according to claim 2, wherein the recording part records user identification information and attribute information of the user.

11. The teaching compatibility determining device according to claim 2, wherein the first detector and the second detector are sensors that detect accelerations and angular velocities of three axes.

12. The teaching compatibility detennining device according to claim 3, wherein the first detector and the second detector are sensors that detect accelerations and angular velocities of three axes.

\* \* \* \* \*